(12) United States Patent
Murphy

(10) Patent No.: US 6,450,973 B1
(45) Date of Patent: Sep. 17, 2002

(54) BIOPSY GUN

(76) Inventor: Kieran P. J. Murphy, 119 Beechdale Rd., Baltimore, MD (US) 21210

( * ) Notice: Subject to any disclaimer, the term of this patent is extended or adjusted under 35 U.S.C. 154(b) by 0 days.

(21) Appl. No.: 09/596,078

(22) Filed: Jun. 16, 2000

(51) Int. Cl.[7] .............................................. A61B 10/00
(52) U.S. Cl. ................... 600/564; 604/164.01; 606/170
(58) Field of Search ................................ 600/562–572; 604/164.01, 164.06; 606/167, 170, 171

(56) References Cited

U.S. PATENT DOCUMENTS

| | | | |
|---|---|---|---|
| 4,177,797 A | * | 12/1979 | Baylis et al. |
| 4,403,617 A | * | 9/1983 | Tretinyak |
| 4,485,815 A | * | 12/1984 | Amplatz et al. |
| 4,798,213 A | * | 1/1989 | Doppelt |
| D300,060 S | * | 2/1989 | Molgaard-Nielsen |
| 4,940,061 A | * | 7/1990 | Terwilliger et al. |
| 4,989,614 A | * | 2/1991 | Dejter, Jr. et al. |
| 5,031,634 A | * | 7/1991 | Simon |
| 5,048,538 A | * | 9/1991 | Terwilliger et al. |
| 5,249,583 A | * | 10/1993 | Mallaby |
| 5,488,958 A | * | 2/1996 | Topel et al. |
| 5,601,559 A | * | 2/1997 | Melker et al. |
| 5,607,389 A | * | 3/1997 | Edwards et al. |
| 5,758,655 A | * | 6/1998 | Como Rodriguez et al. |
| 5,928,238 A | * | 7/1999 | Scarborough et al. |
| 6,022,324 A | * | 2/2000 | Skinner |
| 6,033,411 A | * | 3/2000 | Preissman |

OTHER PUBLICATIONS

Percutaneous Vertebroplasty: State of the Art; Anne Cotten, M.D. et al; Scientific Exhibit, vol. 18, No. 2, Mar.–Apr. 1998; pp. 311–323.*

* cited by examiner

Primary Examiner—Kevin Shaver
Assistant Examiner—Pamela L. Wingood
(74) Attorney, Agent, or Firm—Richard J. Godlewski

(57) ABSTRACT

A kit of parts for taking a biopsy sample from a hard tissue having a needle and a biopsy gun. The needle having an interior shaft and an exterior sleeve forming a tip for piercing hard tissue. The sleeve having a first attachment means and the shaft having a second attachment means complementary to the first attachment means. The biopsy gun having a sampling tip and a third attachment means that is complementary to the second attachment means. In operation, the biopsy gun is placed in the sleeve and secured by the third attachment means and when the gun is fired, a recoil is absorbed by the shaft.

20 Claims, 5 Drawing Sheets

BIOPSY GUN

BACKGROUND OF THE INVENTION

1. Field of the Invention

The present invention relates to a biopsy device (also referred to herein as a "biopsy gun"). In particular, the present invention relates to a biopsy gun used to take biopsy samples from a hard tissue such as a vertebral body.

2. Description of the Prior Art

It is often necessary to obtain a biopsy sample from a patient suspected of having a disease or disorder, such as deterioration of the vertebral body, cancerous tumours or pre-malignant conditions. For example, in vertebroplasty a percutaneous biopsy sample is extracted from the patient prior to the injection of a suitable cement to determine the cause of the deterioration of the vertebral body.

Biopsy samples of vertebral bodies can be taken using a combination of a biopsy needle and a biopsy gun. The needle is inserted into the tissue from which a sample is to be taken, and then the biopsy gun is inserted through the needle shaft to extract the biopsy sample. Generally, the biopsy gun contains an interior sleeve with an open section that receives the tissue sample and is coaxially, slidably engaged with an exterior sleeve. The exterior sleeve may be retracted or pulled back to expose the interior sleeve prior to the sampling and released to contain the sample within the open section. The exterior sleeve of the biopsy gun is connected to a spring or the like that biases the exterior sleeve over the interior sleeve. When the sleeve is pulled back, the spring is compressed and a catch will hold the sleeve to expose the interior sleeve. The sample is taken by releasing the catch which releases the spring causing the exterior sleeve to cover the interior sleeve and slice the tissue sample so that it falls into the open section of the interior sleeve. This action can cause the needle to recoil away from the body that the sample is being taken from.

Overall, it can be seen that conventional biopsy needles and guns for sampling verterbral bodies require a skilled operator to control the positioning of the needle and then control the operation of the biopsy gun while maintaining the position of the needle. This can be awkward for the operator.

Accordingly, it would be desirable to have a biopsy gun or device which facilitated obtaining the biopsy sample.

SUMMARY OF THE INVENTION

It is an object of the present invention to provide a novel biopsy gun which obviates or mitigates at least one of the above-mentioned disadvantages of the prior art.

Accordingly, in one of its aspects, the present invention provides a kit of parts for obtaining a biopsy sample a subject, comprising:
- a needle comprising an interior shaft coaxially disposed within and slidably engaged with respect to an exterior sleeve; the exterior sleeve comprising a first attachment means; the shaft having a second attachment means which cooperates with the first attachment means for releasable engagement of the shaft and the sleeve; and
- a biopsy gun comprising a sampling tip and a third attachment means which cooperates with the first attachment means for releasable engagement of the biopsy gun and the exterior sleeve.

In another of its aspects, the present invention provides a biopsy gun for use with a needle having an interior shaft attached to a first attachment means and an exterior sleeve having a second attachment means for releasable engagement with the first attachment means, the gun comprising:
- a sampling tip; and
- a third attachment means which cooperates with the first attachment means to releasably engage the gun and the sleeve.

In another of its aspects, the present invention provides a kit of parts for taking a biopsy sample from a hard tissue, comprising:
- a needle comprising an interior shaft coaxially disposed within and slidable with respect to an exterior sleeve, the needle comprising a first attachment element;
- a biopsy gun comprising a second attachment element releasably engageable with the first attachment element of the needle.

Thus, an aspect of the invention relates to a kit of parts for taking a biopsy sample from a hard tissue. The kit contains a needle for piercing the hard tissue, with an interior shaft and an exterior sleeve, and a biopsy gun. The interior sleeve has a first attachment means at an end opposite to the tip and the shaft has a second attachment means. The second attachment means is complementary to the first attachment means for releasably securing the shaft to the sleeve. The biopsy gun has a sampling tip longer than the sleeve and a third attachment means substantially identical to the second attachment means, for releasably securing the gun to the sleeve such that when the gun is secured to the sleeve the sampling tip extends therepast and, when fired, a recoil is substantially absorbed by the shaft.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Figure 1:
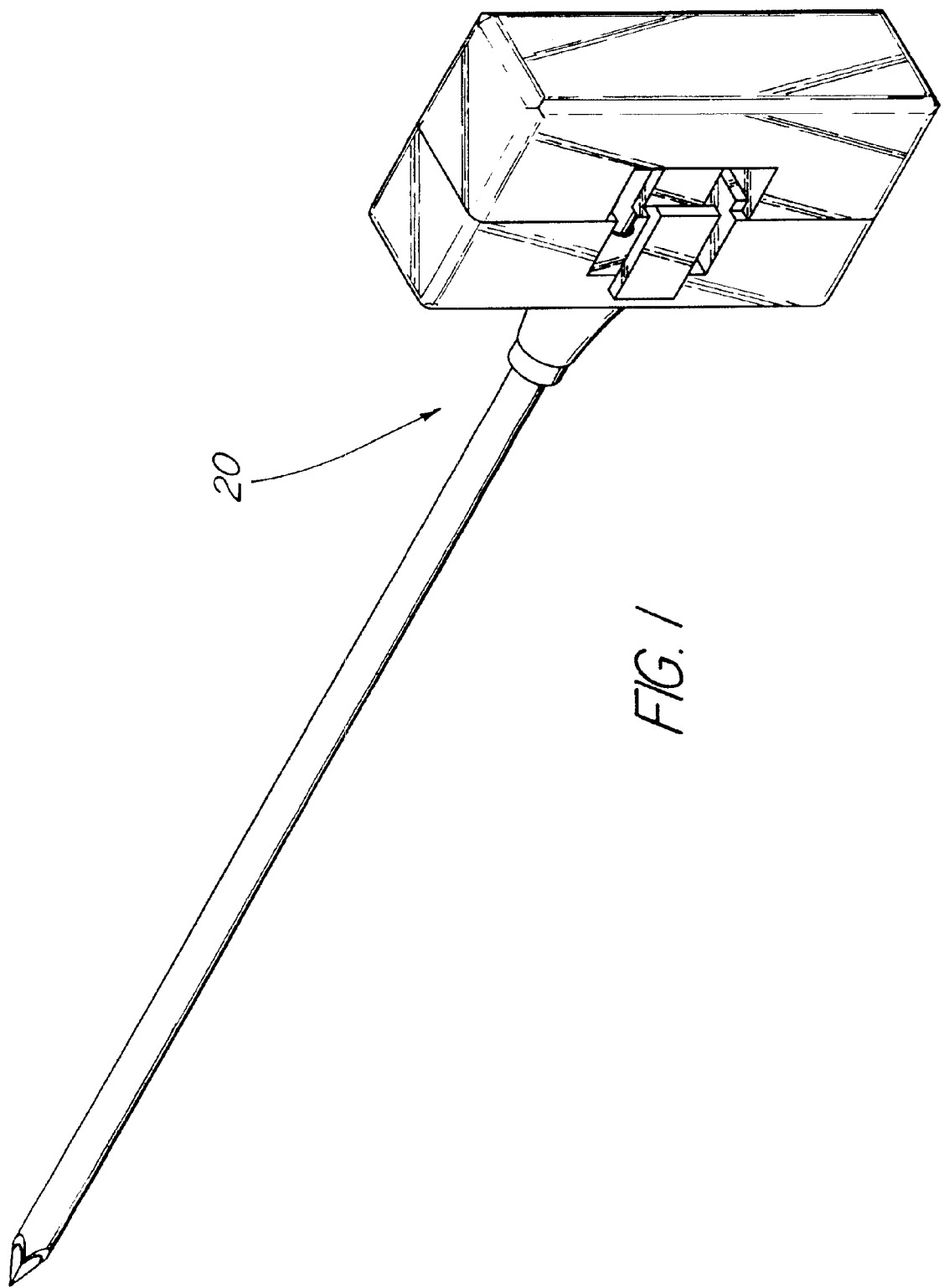
FIG. 1 illustrates an isometric view of a needle with an interior shaft and an exterior sleeve.
Figure 2:
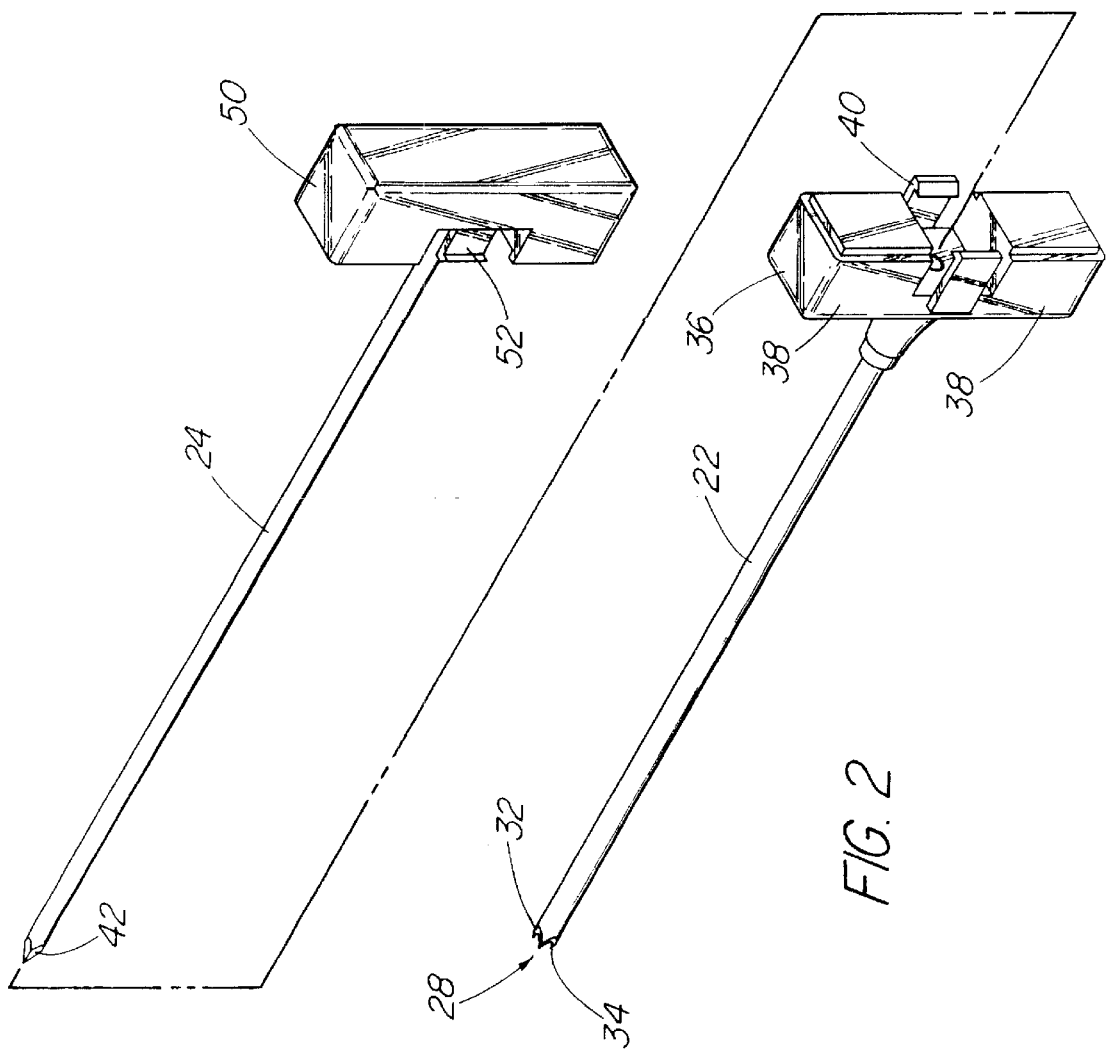
FIG. 2 illustrates an isometric view of the interior shaft of the needle in FIG. 1 removed from the exterior sleeve of the needle.
Figure 3:
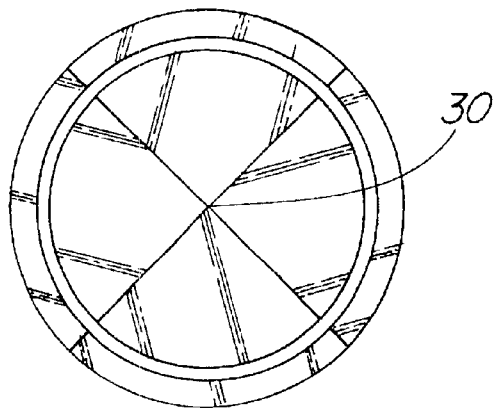
FIG. 3 illustrates an end view of the interior shaft of the needle in FIG. 1.
Figure 4:
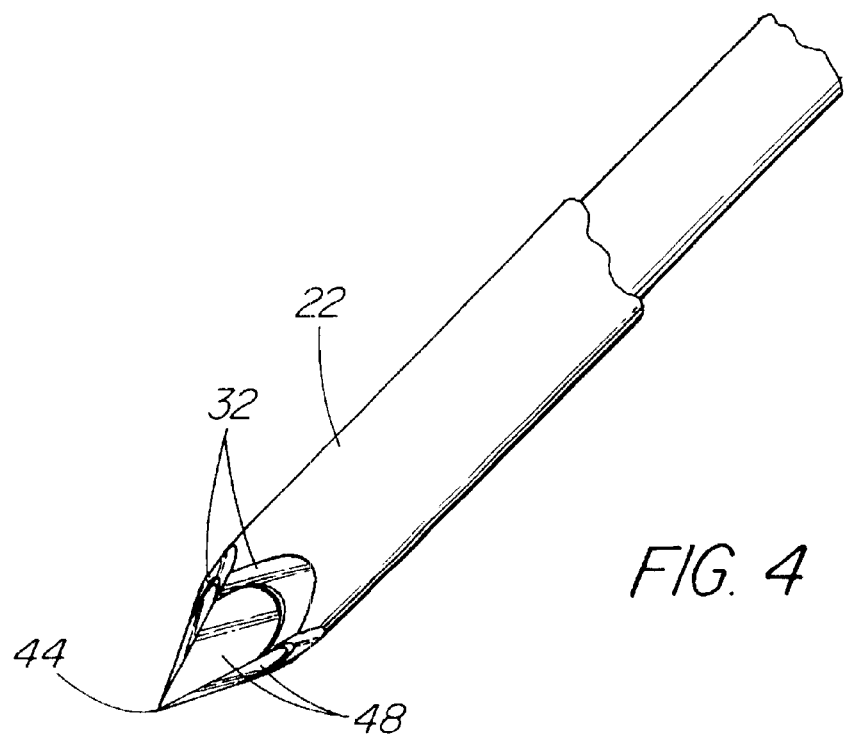
FIG. 4 illustrates a partial isometric view of the tip of the needle in FIG. 1.
Figure 5:
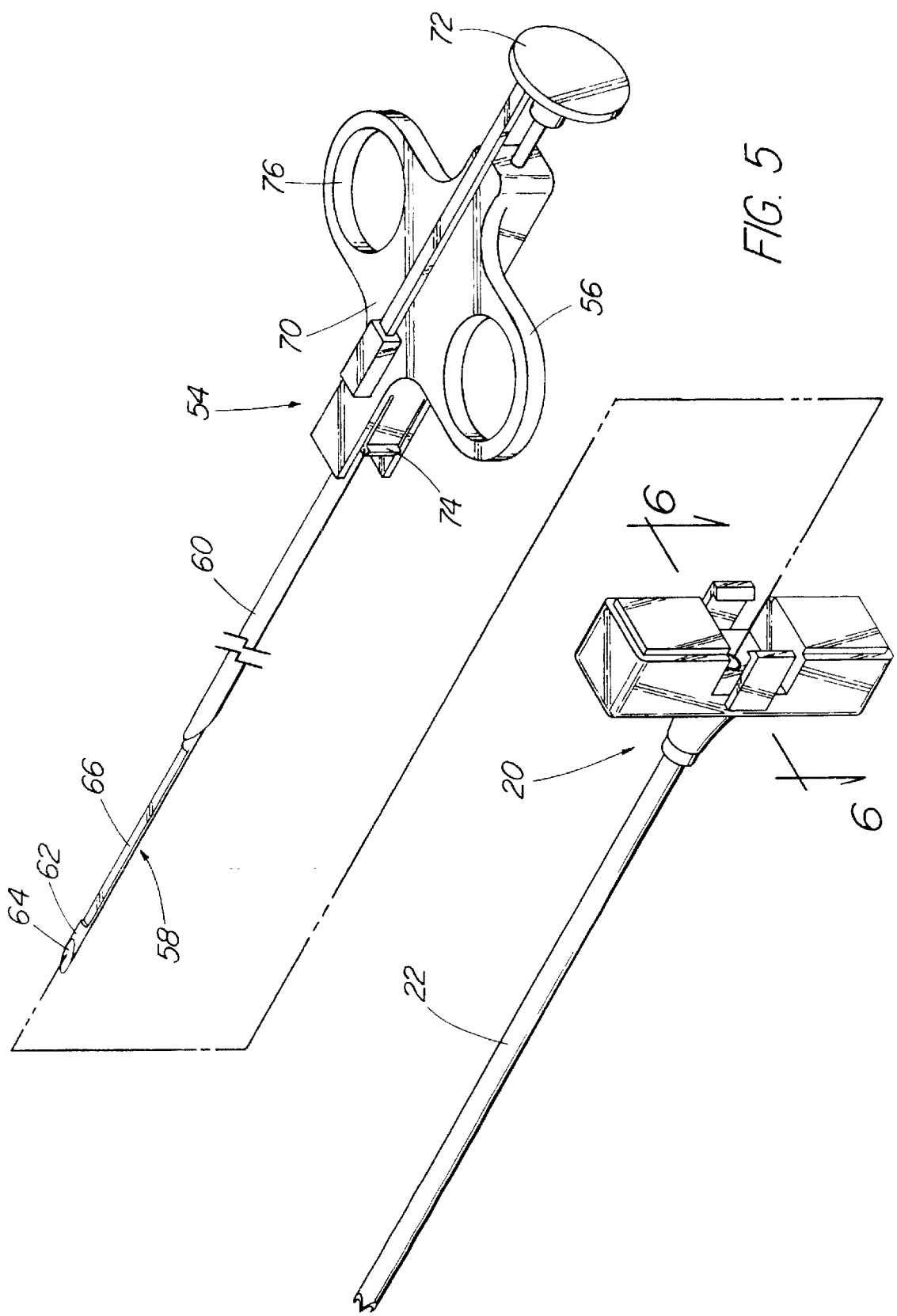
FIG. 5 illustrates an isometric view of a biopsy gun receivable in the exterior sleeve of the needle of FIG. 1.
Figure 6:
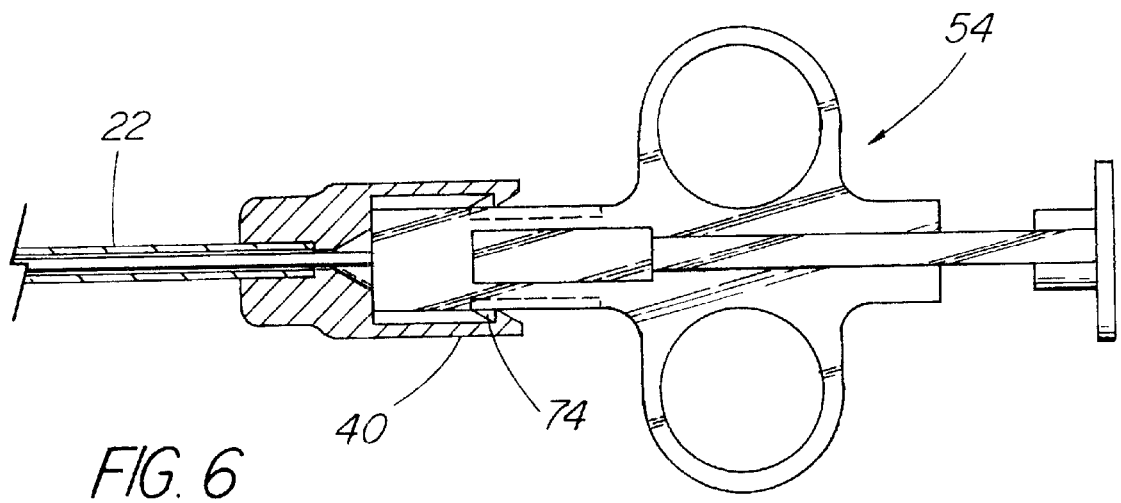
FIG. 6 illustrates an isometric view of a biopsy gun received with the exterior sleeve of the needle of FIG. 1.
Figure 7:
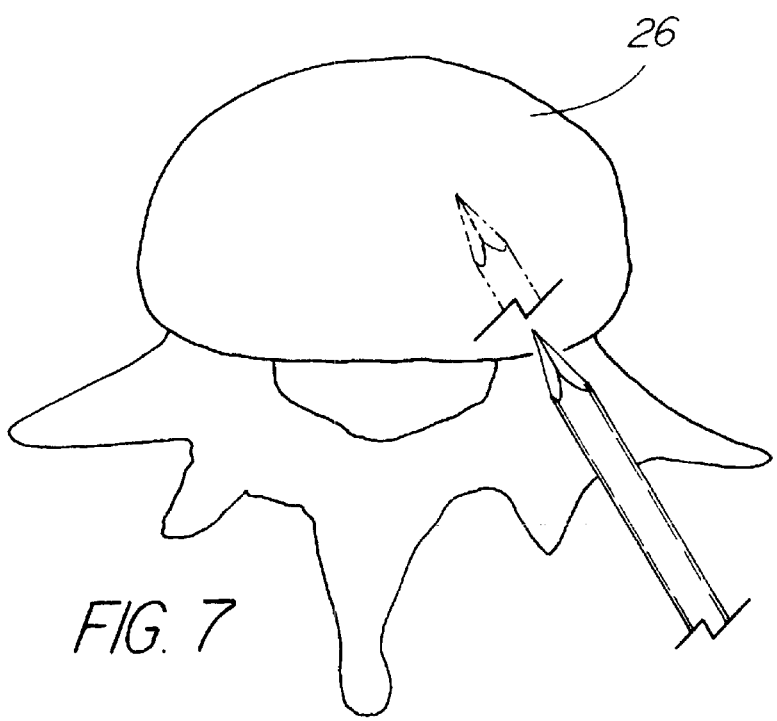
FIG. 7 illustrates an isometric view of a needle receivable in a vertebral body.

With reference to FIGS. 1 to 7, a needle according to an embodiment of the present invention is indicated generally at 20. Needle 20 is preferably used for insertion into a vertebral body or other hard tissue. In a present embodiment needle 20 is surgical grade stainless steel but other suitable materials can be used, as will occur to those of skill in the art. Needle 20 generally consists of a sleeve 22 and a shaft 24 receivably removable within sleeve 22. As shown in FIG. 7, shaft 24 is receivable within sleeve 22 for insertion of needle 20 into a vertebral body 26 via a percutaneous route. Shaft 24 is removable from sleeve 22 to facilitate the engagement of a biopsy gun 54, shown in FIG. 5.

Sleeve 22 is a hollow cylinder with an outlet 28. Sleeve 22 is cylindrically centred about an axis 30. In a present embodiment, the cross-sectional area of sleeve 22 is not reduced at outlet 28, and has four substantially equal, inwardly bevelled surfaces 32 defining outlet 28. Each surface 32 is bevelled toward axis 30. Thus, sleeve 22 has four sharp points 34 at outlet 28. Each sharp point 34 is present at each intersection of two bevelled surfaces 32. Each bevelled surface 32 is at substantially the same angle to axis 30. Preferably, each bevelled surface 32 is at an angle of from about 15° to about 75°. More preferably, each bevelled surface 32 is at an angle of from about 30° to about 60°. It is presently preferred however, that each bevelled surface 32 is at an angle of about 45° to axis 30.

Sleeve 22 is fixed to a first handle 36, at the opposing end to outlet 28, for grasping by the operator. Sleeve 22 can be fixed to first handle 36 by friction fit or other means as will occur to those of skill in the art. Preferably, first handle 36 is a molded polymer but other materials and forming processes can be used. First handle 36 can be any shape suitable for grasping by an operator. According to a present embodiment, first handle 36 has two wings 38 for grasping.

Shaft 24 is generally cylindrical with a tip 42. Tip 42 has four substantially equal, inwardly bevelled faces 48. Each face 48 is bevelled at substantially the same angle as bevelled surfaces 32. Thus, all four bevelled faces 48 intersect at a leading point 44 that protrudes from sleeve 22. When shaft 24 is received within sleeve 22, shaft 24 can be oriented such that each of bevelled faces 48 is aligned with one of bevelled surfaces 32. The bevel angle is substantially identical between shaft 24 and sleeve 22, thus there is no step from tip 42 to sleeve 22, to present four continuous bevelled faces from sleeve 22 to tip 42.

Shaft 24 is fixed to a second handle 50 for grasping by the operator at the opposing end to tip 42. Shaft 24 can be fixed to second handle 50 by friction fit or other means as will occur to those of skill in the art. Preferably second handle 50 is a molded polymer but other materials and forming processes can be used.

First handle 36 comprises first tab 40. Second handle 50 comprises second tab 52. First tab 40 is releasably engageable with second tab 52 of handle 50. In the present embodiment, first tab 40 is an inwardly resilient biased tab. Second tab 52 is a complementary biased tab which engages first tab 40 when shaft 24 is received within sleeve 22. Other suitable attachment means can also be used, as will occur to those of skill in the art, such as a luer lock and other interference fit connection schemes.

Referring now to FIG. 5, a biopsy gun is indicated generally at 54. Biopsy gun 54 generally consists of a body portion 56 and a sampling tip 58. Sampling tip 58 is receivable within sleeve 22 of needle 20 for insertion of sampling tip 58 into a body 26 via percutaneous route.

Sampling tip 58 has a sheath 60 and an insert 62 receivably removable within sheath 60. Insert 62 has a tip 64 and a cavity 66, located adjacent to tip 64, for receiving hard tissue. Sheath 60 is a hollow cylinder with an outlet 68. Sampling tip 58 is fixed to body portion 56 at the opposing end to tip 64. Sampling tip 58 can be fixed to body portion 56 by friction fit or other means as will occur to those of skill in the art.

Body portion 56 consists of a third handle 70, an actuator 72 and a third tab 74. Third handle 70 can be any shape suitable for grasping by an operator. According to a present embodiment third handle 70 has two cyclical hollow portions 76 for receiving the fingers of an operator.

Third tab 74 is operable to releasably attach to first tab 40 of first handle 36. In the present embodiment, third tab 74 is a complementary biased tab which engages first tab 40 when biopsy gun 54 is received within sleeve 22, as shown in FIG. 6.

In a present embodiment, actuator 72 is retractable and integrally coupled to sheath 60. Actuator 72 is spring loaded and is operable to slidingly retract sheath 60 along insert 62, in the opposite direction from tip 64, for uncovering cavity 66 when sampling tip 58 is releasably engaged in vertebral body 26. When actuator 72 is retracted, sheath 60 is moved along insert 62 away from tip 64 and held in a locked position. This motion causes cavity 66 to be revealed and operable to receive hard tissue.

When actuator 72 is released sheath 60 is projected along insert 62 until it reaches tip 64. This motion causes cavity 66 to be covered by sheath 60.

The operation of biopsy gun 54 will now be described with reference to the foregoing and, particularly, attached FIGS. 5–7. Needle 20 is inserted into vertebral body 26 via a percutaneous route. Second tab 52 is detached from first tab 40 and shaft 24 is slidably removed from sleeve 22. Sleeve 22 is now operable to receive biopsy gun 54. Biopsy gun 54 is inserted into vertebral body 26 by slidably engaging sampling tip 58 in sleeve 22. Third tab 74 is releasably attached to first tab 40.

Once biopsy gun 54 has been inserted in vertebral body 26, actuator 72 is retracted from body portion 56 and sheath 60 is retracted along insert 62 away from tip 64. When actuator 72 is locked in a retracted position it holds sheath 60 in a position that reveals cavity 66 on insert 62. Once revealed, cavity 66 is operable to receive hard tissue. Actuator 72 may then be released and sheath 60 is fired along insert 62 to tip 64. As sheath 60 passes over cavity 66 the edge of outlet 68 slices through the hard tissue. A sample of hard tissue remains enclosed in cavity 66.

In order to remove biopsy gun 54 from vertebral body 26, third tab 74 is detached from first tab 40. Biopsy gun 54 is now operable to slidingly move out of vertebral body 26 through sleeve 22. The hard tissue sample can be removed from cavity 66 by repeating the above method of retracting actuator 72.

While the embodiment discussed herein is directed to a particular implementation of the invention, it will be apparent that variations of this embodiment are within the scope of the invention. For example, first tab, second tab and third tab may be other complementary locking devices, such as male and female luer locks. First handle, second handle and third handle may be any shape suitable to be grasped and securely held by an operator. The actuator may be any device suitable for retracting and firing the sheath along the insert and may work in combination with the third handle so that the third handle is spring loaded and operable to retract the sheath and the actuator is coupled to the third handle and is operable to release the sheath. Thus, while the present invention has been described with reference to preferred and specifically illustrated embodiments, it will of course be understood by those skilled in the arts that various modifications to these preferred and illustrated embodiments may be made without departing from the spirit and scope of the invention.

All publications, patents and patent applications referred to herein are incorporated by reference in their entirety to the same extent as if each individual publication, patent or patent application was specifically and individually indicated to be incorporated by reference in its entirety.

What is claimed is:

1. A kit of parts for obtaining a biopsy sample from a subject, comprising:

a needle comprising an interior shah coaxially disposed within and slidably engaged with respect to an exterior sleeve; the exterior sleeve comprising a first attachment means; the shaft having a second attachment means which cooperates with the first attachment means for releasable engagement of the shaft and the sleeve; and a biopsy gun comprising a sampling tip and a third attachment means which cooperates with the first attachment means for releasable engagement of the biopsy gun and the exterior sleeve.

2. The kit defined in claim 1, wherein the biopsy gun further comprises a first actuator for moving the sampling tip from a first retracted position to a second extended position.

3. The kit defined in claim 2, wherein the biopsy gun further comprises a second actuator for moving the sampling tip from the second extended position to the first retracted position.

4. The kit defined in claim 3, wherein first actuator and the second actuator are independently operable.

5. The kit defined in claim 1, wherein at least one of the first attachment means, the second attachment means and the third attachment means comprises a biasing member.

6. The kit defined in claim 1, wherein each of the first attachment means, the second attachment means and the third attachment means comprises a biasing member.

7. The kit defined in claim 1, wherein at least one of the first attachment means, the second attachment means and the third attachment means comprises a luer lock.

8. The kit defined in claim 1, wherein each of the first attachment means, the second attachment means and the third attachment means comprises a luer lock.

9. The kit defined in claim 1, wherein the sampling tip comprises a cavity operable to receive hard tissue.

10. The kit defined in claim 1, wherein the sampling tip comprises a cavity operable to receive hard tissue, the cavity being exposed in the first retracted position of the sampling tip and covered in the second retracted position.

11. A biopsy gun for use with a needle having an interior shaft attached to a first attachment means and an exterior sleeve having a second attachment means for releasable engagement with the first attachment means, the gun comprising:

a sampling tip, wherein the sampling tip comprises a cavity operable to receive hard tissue; and a third attachment means which cooperates with the second attachment means to releasably engage the gun and the sleeve.

12. The biopsy gun defined in claim 11, further comprising a first actuator for moving the sampling tip from a first retracted position to a second extended position.

13. The biopsy gun defined in claim 12, further comprising a second actuator for moving the sampling tip from the second extended position to the first retracted position.

14. The biopsy gun defined in claim 13, wherein the first actuator and the second actuator are independently operable.

15. The biopsy gun defined in claim 11, wherein at least one of the first attachment means, the second attachment means and the third attachment means comprises a biasing member.

16. The biopsy gun defined in claim 11, wherein each of the first attachment means, the second attachment means and the third attachment means comprises a biasing member.

17. The biopsy gun defined in claim 11, wherein at least one of the first attachment means, the second attachment means and the third attachment means comprises a luer lock.

18. The biopsy gun defined in claim 11, wherein each of the first attachment means, the second attachment means and the third attachment means comprises a luer lock.

19. The biopsy gun defined in claim 11, wherein the cavity is exposed in the first retracted position of the sampling tip and covered in the second retracted position.

20. A kit of parts for taking a biopsy sample from a hard tissue, comprising:

a needle comprising an external sleeve and an interior shaft coaxially disposed within and slidable with respect to the exterior sleeve, the needle comprising a first attachment element; and a biopsy gun separate from the needle and comprising a second attachment element releasably engageable with the first attachment element of the needle.

* * * * *